(12) United States Patent
Yamamoto (10) Patent No.: US 8,636,135 B2
(45) Date of Patent: Jan. 28, 2014

(54) SORTING APPARATUS

(75) Inventor: Hiroki Yamamoto, Kagawa (JP)

(73) Assignee: Unicharm Corporation, Shikokuchuo-Shi, Ehime-Ken (JP)

( * ) Notice: Subject to any disclaimer, the term of this patent is extended or adjusted under 35 U.S.C. 154(b) by 0 days.

(21) Appl. No.: 13/520,841

(22) PCT Filed: Jan. 7, 2011

(86) PCT No.: PCT/JP2011/050203
§ 371 (c)(1),
(2), (4) Date: Sep. 19, 2012

(87) PCT Pub. No.: WO2011/083856
PCT Pub. Date: Jul. 14, 2011

(65) Prior Publication Data
US 2013/0001042 A1 Jan. 3, 2013

(30) Foreign Application Priority Data
Jan. 9, 2010 (JP) ................... 2010-003435

(51) Int. Cl.
*B65G 47/10* (2006.01)
*B65G 47/46* (2006.01)

(52) U.S. Cl.
USPC ................... 198/369.2; 198/367.1

(58) Field of Classification Search
USPC ......... 198/367.1, 369.1, 369.2, 370.12, 689.1
See application file for complete search history.

(56) References Cited

U.S. PATENT DOCUMENTS

| | | | | |
|---|---|---|---|---|
| 6,419,217 B1* | 7/2002 | Hartmann et al. | ......... | 198/369.2 |
| 6,708,813 B2* | 3/2004 | Takahashi | ......... | 198/369.2 |
| 6,868,958 B2* | 3/2005 | Betti et al. | ......... | 198/435 |
| 2003/0019719 A1* | 1/2003 | Wiehler | ......... | 198/369.2 |
| 2010/0084246 A1* | 4/2010 | Kalm et al. | ......... | 198/617 |

FOREIGN PATENT DOCUMENTS

| | | |
|---|---|---|
| JP | 7051633 A | 2/1995 |
| JP | 2001089003 A | 4/2001 |
| JP | 2006061767 A | 3/2006 |
| JP | 2009227460 A | 10/2009 |

OTHER PUBLICATIONS

International Search Report and Written Opinion for PCT/JP2011/050203, dated Apr. 5, 2011.

* cited by examiner

*Primary Examiner* — James R Bidwell
(74) *Attorney, Agent, or Firm* — Lowe Hauptman & Ham, LLP (57) ABSTRACT

The belt conveyer 10 includes guide members 100F and 100R. The guide members 100F and 100R are disposed between the endless belts 13A and 13B. The belt conveyer has a suction box 81 and a blower 91. The belt conveyor 10 becomes able to suction the air via the conveyance surface 10A that is the workpiece holding surface.

8 Claims, 5 Drawing Sheets

SORTING APPARATUS

RELATED APPLICATIONS

The present application is a National Phase of International Application Number PCT/JP2011/050203, filed Jan. 7, 2011, and claims priority from Japanese Application Number 2010-003435, filed Jan. 9, 2010.

TECHNICAL FIELD

The present invention relates to a sorting apparatus configured to sort out sheet-like workpiece formed by piling up a plurality of unwoven fabrics to a predetermined conveyance destination.

BACKGROUND ART

Conventionally, in a process of manufacturing a product, there is widely used a sorting apparatus configured to sort out a sheet-like workpiece sequentially conveyed at certain intervals to a predetermined conveyance destination. For example, a sorting apparatus discussed in Japanese Patent Application Publication No. 2001-89003 (Pages 3 to 4, and FIGS. 2 and 4) uses a flap configured to sort out a conveyance destination of a workpiece (plate on which a photosensitizing agent is applied) sequentially conveyed by a conveyor according to the workpiece's quality and other criteria.

This flap, which is of box-like triangular pyramid, is installed in the middle of the conveyer. The top of the pyramid is positioned upstream of the conveyor. Normally, the workpiece passes above the top surface of the flap. In the case where the workpiece is determined as "poor quality", the flap rotates upward having its downstream part fixed as an axis of rotation. When the flap rotates upward, the conveyed workpiece abuts the bottom surface of the flap and is sorted out to another conveyer which is built under the flap.

However, when the sorting apparatus including the above-described flap is used to sort out the workpiece formed by piling up a plurality of unwoven fabrics, which are constituents, such as a disposable diaper and a sanitary napkin, there arises a problem that sorting cannot be appropriately performed.

Specifically, when the workpiece conveyed at high speed is sorted out to another conveyor built under the flap, since the flap rotates upwardly, the distal end of the workpiece once leaves the conveyor then abuts the bottom surface of the flap like a collision. A soft workpiece is easily bent when the workpiece collides at high speed with the bottom surface of the flap. This easily arises a problem that the workpiece is unable to pass the sorting apparatus readily causes a jam.

Also, at a lower part of the flap, i.e., a portion where a conveyance destination is sorted out, there is a certain air gap between a conveyor of the conveyance source and a conveyor of a conveyance destination. This easily leads to a problem that the distal end of the workpiece goes into the space, thus causing a jam.

Therefore, the present invention has an objective to provide a sorting apparatus capable to sorting the workpiece more surely and smoothly based on the workpiece's quality and other criteria even when the sheet-like workpiece so formed that a plurality of unwoven fabrics, constituent components of a disposable diaper and a sanitary napkin, for example, are piled up is conveyed at high speed.

SUMMARY OF THE INVENTION

The feature of the present invention is summarized in that a sorting apparatus (sorting apparatus 1) configured to sort out a sheet-like workpiece (workpiece W) so formed that a plurality of unwoven fabrics are piled up to a second conveyance route (conveyance route R2) or a third conveyance route (conveyance routes R3, R4) from a first conveyance route (conveyance route R1), the apparatus including a conveyor mechanism (belt conveyers 10, 20, 30) configured to convey the workpiece from the first conveyance route to the second conveyance route while the workpiece is held, the conveyor mechanism abutting one surface of the workpiece and having the workpiece holding surface (conveyance surface 10A, 20A, 30A), and a transferring mechanism (guide member 100F, 100R, rotation supporting unit 110F, 110R) configured to transfer the workpiece conveyed from the first conveyance route by the conveyor mechanism to the third conveyance route, wherein the third conveyance route is branched off from between the first conveyance route and the second conveyance route, the conveyor mechanism is continued over the first conveyance route and the second conveyance route, and the transferring mechanism pushes out the workpiece held for conveyance by the conveyor mechanism from the workpiece holding surface toward the third conveyance route thereby to transfer the workpiece to the third conveyance route.

DESCRIPTION OF THE EMBODIMENTS

Subsequently, embodiments of a sorting apparatus according to the present invention will be explained with reference to the diagrams. In the following description of the diagrams, the identical or similar portions are assigned with the identical or similar numerals. However, it should be noted that the diagrams are schematic and ratios of the respective dimensions do not justify the actual ones.

Therefore, the specific dimensions, etc., should be determined in consideration of the following explanations. Moreover, it is needless to say that relations and ratios among the respective dimensions differ among the diagrams.

Embodiment

An overview of a sorting apparatus 1 according to an embodiment of the present invention will be explained.

Figure 1:
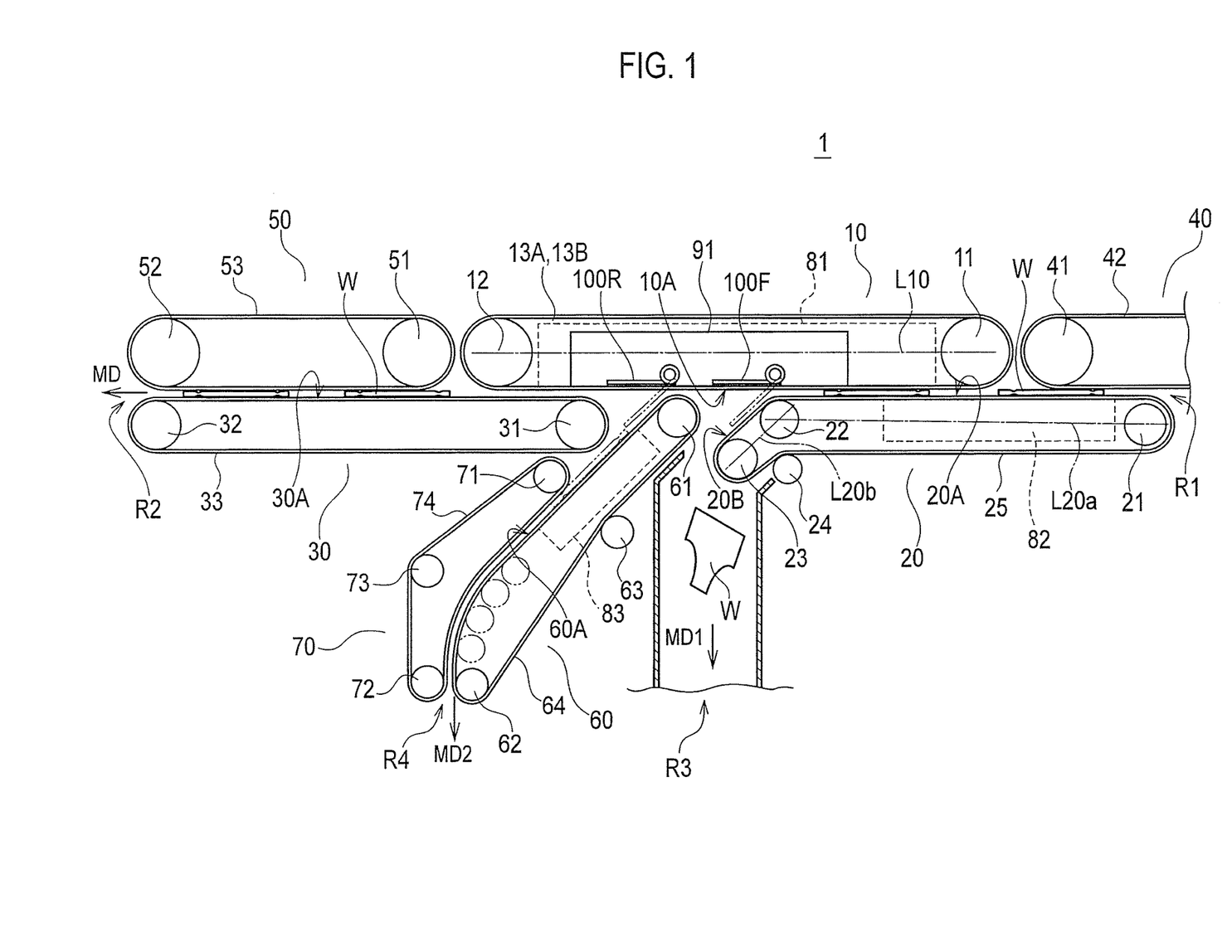
FIG. 1 is a side view in which a sorting apparatus 1 according to an embodiment of the present invention is seen from a direction perpendicular to a conveyance direction MD.

FIG. 1 is a side view in which the sorting apparatus 1 according to the embodiment of the present invention is seen from a direction perpendicular to a conveyance direction MD.

The sorting apparatus 1 sorts out a sheet-like workpiece W formed by piling up a plurality of unwoven fabrics, which are constitutents, such as a disposable diaper and a sanitary napkin to a plurality of conveyance routes along a manufacturing step while the workpiece W is held.

The sorting apparatus 1 includes belt conveyors 10, 20 and 30 that are configured to hold for conveyance of the workpiece W and abut one surface of the workpiece W.

The belt conveyor 10 includes a roller 11 disposed upstream of the conveyance direction MD, a roller 12 disposed downstream, and an endless belt 13 passing around the rollers 11 and 12. The endless belt 13 has a plurality of through holes not shown.

The rollers 11 and 12 are disposed so that the rotation shafts of the rollers 11 and 12 are parallel to a direction CD perpendicular to the conveyance direction MD. An imaginary line linking the rotation shaft of the roller 11 and that of the roller 12 is disposed substantially parallel to the conveyance direction MD. The surface of the endless belt 13 abuts to one surface of the workpiece W and configures a conveyance surface 10A on which the workpiece W is held for conveyance. The conveying surface 10A configures a workpiece holding surface.

The belt conveyor 10 includes a suction box 81 configured to suction external air from the through holes of the endless belt 13, inside the endless belt 13 passing around the rollers 11 and 12. As a result, the belt conveyor 10 is able to convey the workpiece W, which is tightly adhered to the conveyance surface 10A. The belt conveyor 10 also includes a blower 91 configured to send air to the workpiece W through the through holes of the endless belt 13, inside the endless belt 13 passing around the rollers 11 and 12. The belt conveyor 10 will be explained in detail later.

The belt conveyor 20 includes a roller 21 disposed upstream of the conveyance direction MD, a roller 23 disposed downstream, a roller 22 disposed between the roller 21 and the roller 23, and an endless belt 25 passing around the rollers 21, 22, and 23. The endless belt 25 has a plurality of through holes not shown.

The rollers 21 to 23 are disposed so that rotation shafts of the rollers 21 to 23 are parallel to the perpendicular direction CD. A virtual line L20a linking the rotation shaft of the roller 21 and that of the roller 22 cross a virtual line L20b linking the rotation shaft of the roller 22 and that of the roller 23.

That is, the roller 23 is disposed to be deviated from the roller 21 and the roller 22 in the conveyance direction MD. Therefore, the conveyance surface of the endless belt 25 of the belt conveyor 20 is bent. Upstream of the conveyance direction MD of the belt conveyor 20, a conveyance surface 20A parallel to the conveyance surface 10A of the belt conveyor 10 is formed. Downstream of the conveyance direction MD, a conveyance surface 20B, which extends away from the conveyance surface 10A of the belt conveyor 10, is formed. The conveyance surface 20A and the conveyance surface 20B configure a workpiece holding surface.

The belt conveyor 20 includes a suction box 82 configured to suction external air from the through holes of the endless belt 25, inside the endless belt 25 passing around the rollers 21, 22, and 23. As a result, the belt conveyor 20 is able to convey the workpiece W, which is tightly adhered to the conveyance surface 20A.

The belt conveyor 30 includes a roller 31, a roller 32, and an endless belt 33 passing around the rollers 31 and 33. The positional relation between the rollers 31 and 32 is the same as that of the belt conveyors 10 and 20. The surface of the endless belt 33 abuts one surface of the workpiece W and configures a conveyance surface 30A on which the workpiece W is held for conveyance. The conveyance surface 30A configures a workpiece holding surface.

The belt conveyor 30 is disposed further downstream of the conveyance direction MD than the belt conveyor 20 at the predetermined interval so that the conveyance surfaces 20A and 30A are on the substantially same plane surface.

Between the belt conveyors 20 and 30, a belt conveyor 60 including a conveyance surface 60A extending away from the conveyance surface 10A of the belt conveyor 10 is disposed.

The belt conveyor 60 includes a roller 61, a roller 62, and a roller 63. An endless belt 64 passes around the rollers 61, 62, and 63. The endless belt 64 has a plurality of through holes not shown. The surface of the endless belt 64 abuts one surface of the workpiece W and configures a conveyance surface 60A on which the workpiece W is held for conveyance. The conveyance surface 60A configures a workpiece holding surface.

The belt conveyor 60 includes a suction box 83 configured to suction external air from the through holes of the endless belt 64, inside the endless belt 64 passing around the rollers 61, 62, and 63. As a result, the belt conveyor 60 is able to convey the workpiece W, which is tightly adhered to the conveyance surface 60A.

At a position facing the conveyance surface 60A of the belt conveyor 60, a belt conveyor 70 is disposed. The belt conveyor 70 includes a roller 71, a roller 22, and a roller 73. An endless belt 74 passes around the rollers 71, 72, and 73. The surface of the endless belt 74 abuts one surface of the workpiece W and configures a conveyance surface 70A on which the workpiece W is held for conveyance. The conveyance surface 70A configures a workpiece holding surface.

In this embodiment, the belt conveyors 10, 20 and 30 configure a conveyor mechanism. Also, in this embodiment, the belt conveyors 60 and 70 configure a sub conveyor mechanism.

The conveyance surface 10A of the belt conveyor 10 and the conveyance surface 20A of the belt conveyor 20 configure a conveyance route R1. The conveyance surface 10A of the belt conveyor 10 and the conveyance surface 30A of the belt conveyor 30 configure a conveyance route R2. In this embodiment, a direction where the workpiece W is conveyed from the conveyance route R1 to the conveyance route R2 is regarded as the conveyance direction MD. The conveyance surface 20B configures a conveyance route R3 extending in the conveyance direction MD1. The conveyance surface 60A and conveyance surface 70A configure a conveyance route R4 extending in the conveyance direction MD2.

In this embodiment, the conveyance route R1 is equivalent to a first conveyance route. The conveyance route R2 is equivalent to a second conveyance route. The conveyance routes R3 and R4 configure a third conveyance route.

The sorting apparatus 1 may include a belt conveyor 40 that is located further upstream of the conveyance direction MD than the belt conveyor 10 and located at a position to face the conveyance surface 20A of the belt conveyor 20. The belt conveyor 40 includes a roller (not shown) disposed upstream of the conveyance direction MD, a roller 41 disposed downstream, and an endless belt 42 passing around the roller and the roller 41.

The sorting apparatus 1 may further include a belt conveyor 50 that is located further downstream of the conveyance direction MD than the belt conveyor 10 and located at a position to face the conveyance surface 30A of the belt conveyor 30. The belt conveyor 50 includes a roller 51 disposed upstream of the conveyance direction MD, a roller 52 disposed downstream, and an endless belt 53 passing around the rollers 51 and 52.

Figure 2:
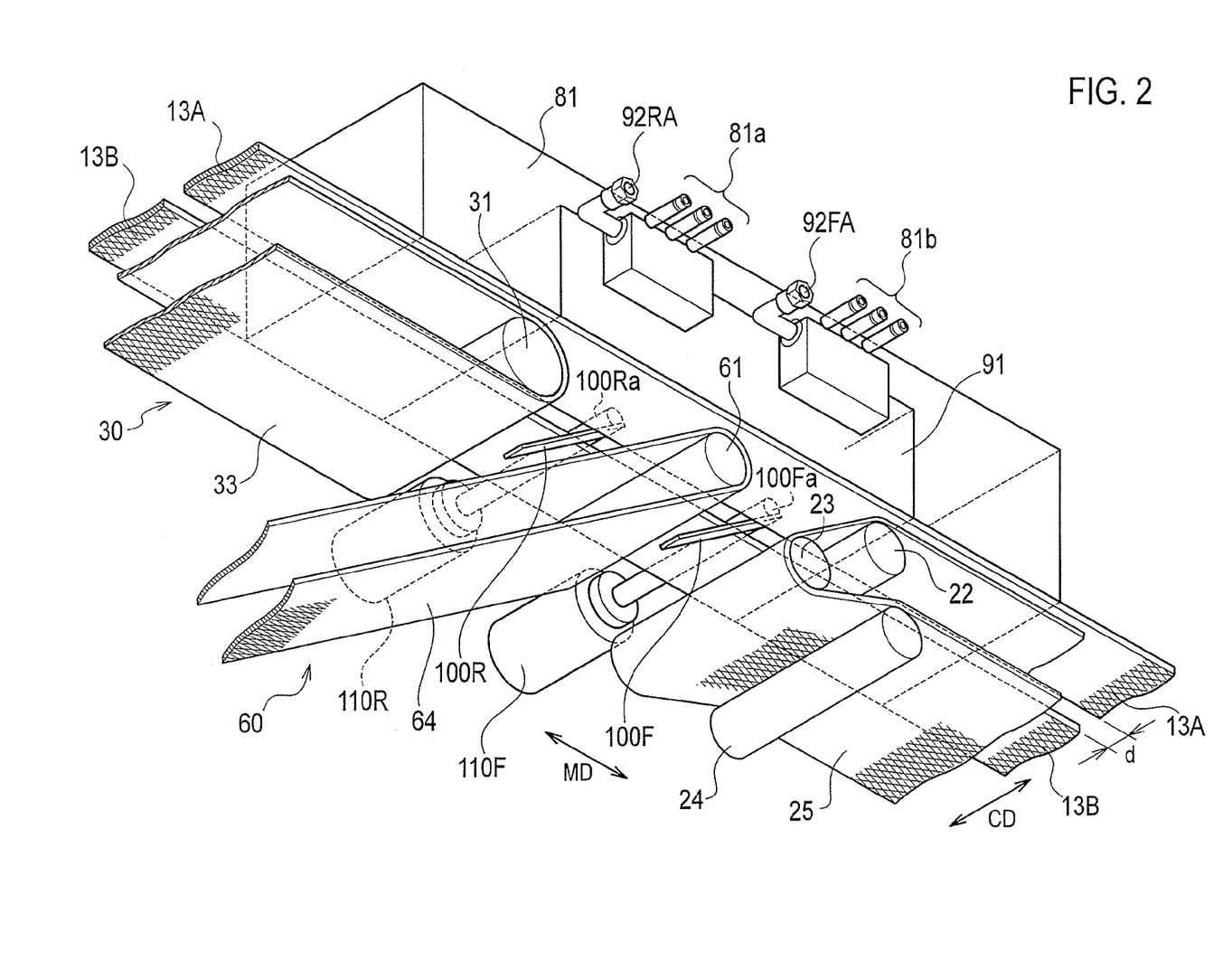
FIG. 2 is a perspective view of the sorting apparatus 1 according to this embodiment.
Figure 3:
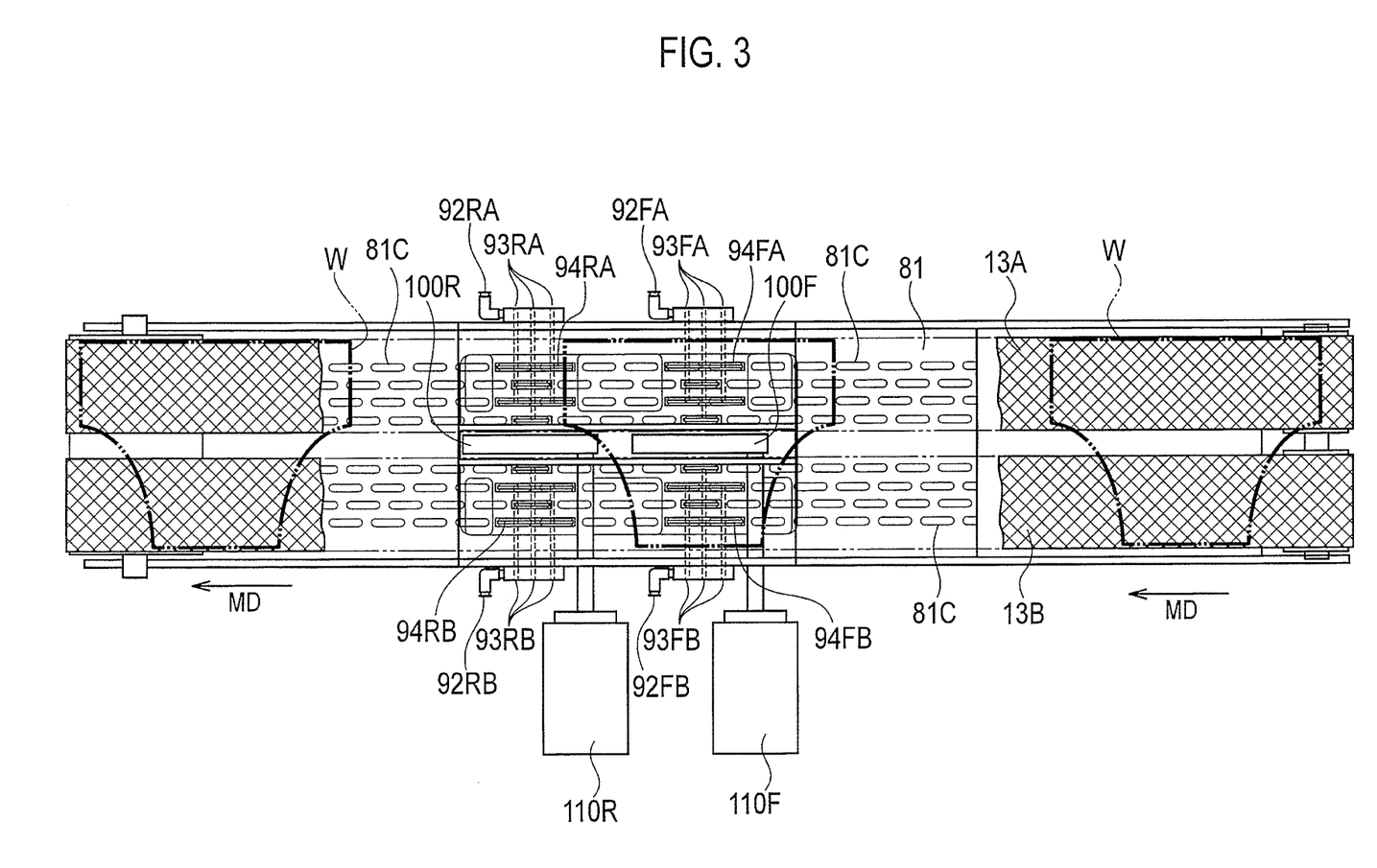
FIG. 3 is a plain view in which the sorting apparatus 1 according to this embodiment is seen from a workpiece holding surface side of endless belts 13A and 13B.
Figure 4:
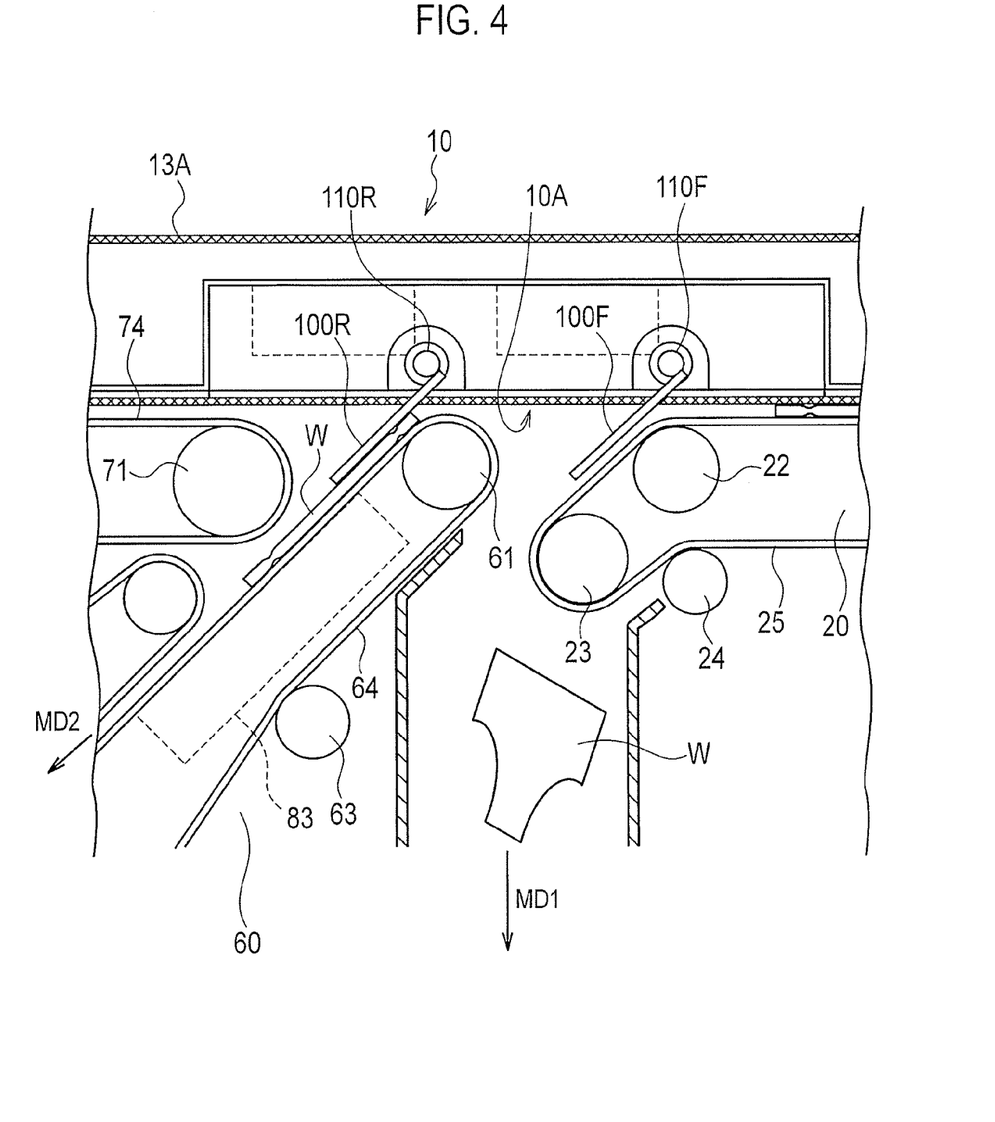
FIG. 4 is an enlarged side view showing a surrounding area of guide members 100F and 100R of the sorting apparatus 1 according to this embodiment in an enlarged manner.

Subsequently, the configuration of the belt conveyor 10 will be specifically explained. FIG. 2 is a perspective view of the sorting apparatus 1 according to this embodiment. FIG. 3 is a plain view in which the cutaway endless belt 13 of the sorting apparatus 1 according to this embodiment is seen from the workpiece holding surface side. FIG. 4 is an enlarged side view showing a surrounding area of guide members 100F and 100R of the sorting apparatus 1 according to this embodiment in an enlarged manner.

The endless belt 13 includes endless belts 13A and 13B. The endless belts 13A and 13B are disposed in parallel along the direction CD perpendicular to the conveyance direction MD at a predetermined interval d.

The belt conveyor 10 includes a guide member 100F and a guide member 100R. The guide member 100F and the guide member 100R are disposed nearer to the center than the endless belt 13A and the endless belt 13B as a workpiece holding unit configured to hold the workpiece W across the direction CD perpendicular to the conveyance direction MD. That is, the guide member 100F and the guide member 100R are disposed between the endless belt 13A and the endless belt 13B.

A rotation supporting unit 110F is coupled to the guide member 100F. A rotation supporting unit 110R is coupled to the guide member 100R. The rotation supporting unit 110F and the rotation supporting unit 110R rotatably support upstream side ends 100Fa and 100Ra of the guide members 100F and 100R. As a result of rotation by the rotation supporting unit 110F and the rotation supporting unit 110R, the guide member 100F and the guide member 100R can project themselves from where the guide members 100F and 100R are housed further inside the endless belts 13A and 13B than the conveyance surface 10A, which acts as a workpiece holding surface, toward the conveyance route R3 or R4. When the guide member 100F and the guide member 100R are projected toward the conveyance route R3 or R4, these guide members 100F and 100R transfer the workpiece W, which is held on the conveyance surface 10A for conveyance, i.e., the workpiece holding surface, to either the conveyance route R3 or R4.

In this embodiment, the guide member 100F, the guide member 100R, the rotation supporting unit 110F, and the rotation supporting unit 110R configure a transferring mechanism configured to transfer the workpiece W from the conveyance routes R1 to R2, or from the conveyance routes R1 to R3 or R4.

The belt conveyor 10 includes a suction box 81 and a blower 91. A plurality of suction holes 81c are formed on the entire surface of the endless belt sides 13A and 13B of the suction box 81. A suction tube 81a and a suction tube 81b communicated to a suction pump (not shown) configured to suction air inside the suction box 81 are coupled to the suction box 81. As a result, the belt conveyor 10 becomes able to suction the air via the surface of the endless belts 13A and 13B, i.e., the conveyance surface 10A that is the workpiece holding surface.

The blower 91 is disposed inside the suction box 81. A ventilation hole 94FA, a ventilation hole 94RA, a ventilation hole 94FB, and a ventilation hole 94RB are formed in one portion of the blower 91 and the endless belt sides 13A and 13B of the suction box 81. Specifically, these ventilation holes are formed at positions corresponding to the guide member 100F and the guide member 100R which are housed further inside the endless belts 13A and 13B than the conveyance surface 10A that is the workpiece holding surface. A ventilation tube 92FA, a ventilation tube 92FB, a ventilation tube 92RA, and a ventilation tube 92RB each configured to take air from an air blower (not shown) installed outside are coupled to the blower 91.

The ventilation strength of the blower 91 is set to be greater than the suction power to suction air inside the suction box 81. Therefore, although the blower 91 is disposed inside the suction box 81, the blower 91 is able to blow air from the surface of endless belts 13A and 13B, i.e., the conveyance surface 10A that is the workpiece holding surface, to the conveyance route R3 or R4.

Figure 5:
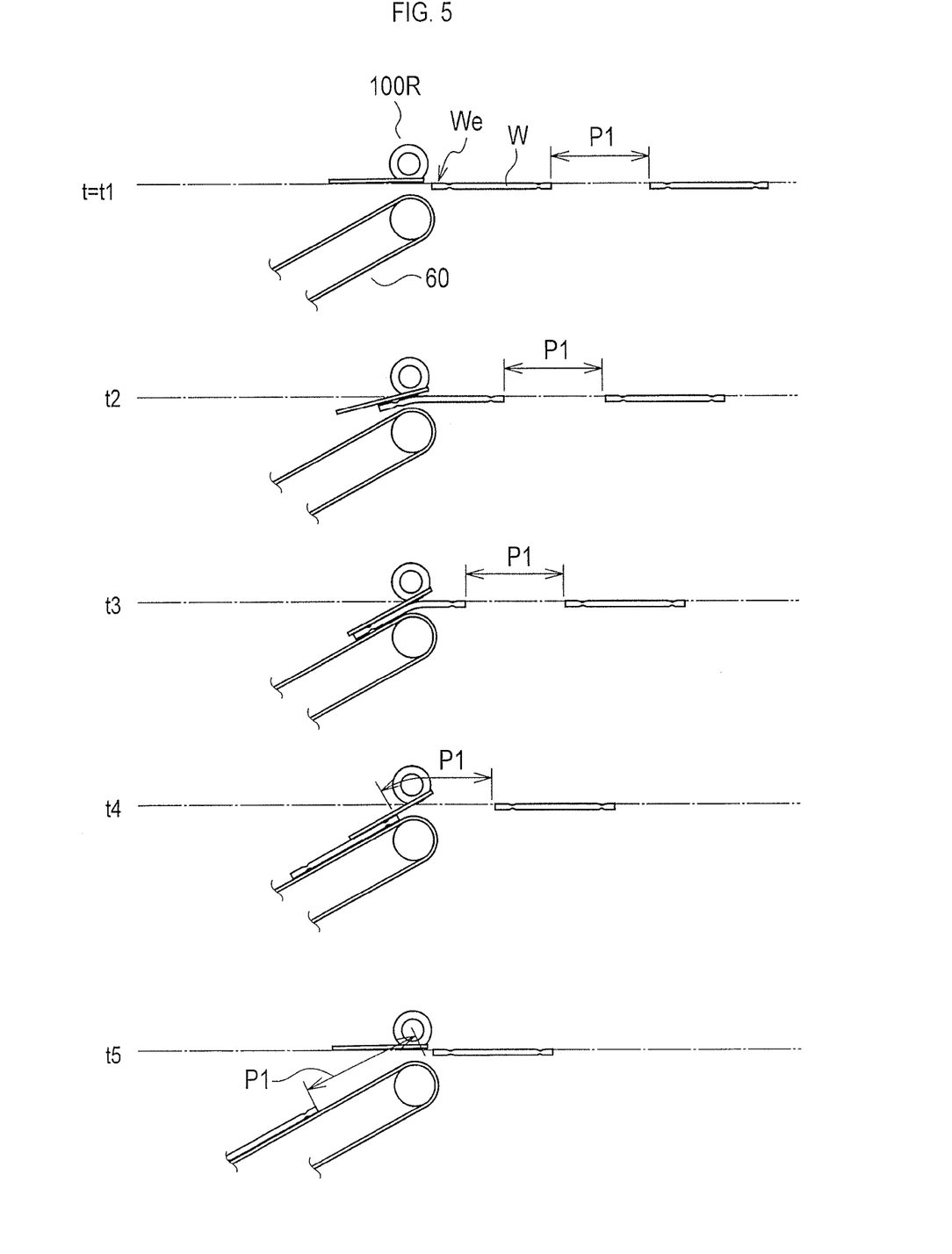
FIG. 5 is an explanatory view explaining a timing at which the sorting apparatus 1 according to this embodiment sorts out a workpiece W.

FIG. 5 is an explanatory view explaining a timing at which the sorting apparatus 1 according to this embodiment sorts out the workpiece W. FIG. 5 shows a movement of the guide member 100R at times t1 to t5 at equal intervals, and a position of the workpiece W. In this embodiment, the setting is such that the guide member 100 transfers the workpiece W to conveyance surface 60A (i.e., the conveyance route R4) in the state where a downstream side end We positioned downstream of the conveyance direction of the conveyed workpiece W abuts at least one of the conveyance surface 10A that is the workpiece holding surface or an abutment surface between the belt conveyor 60 and the workpiece W (see time t2).

The guide member 100R is set to return to an initial position after transferring the first workpiece W to the conveyance surface 60A (conveyance route R4) until the downstream side end We of the next workpiece W conveyed at a pitch P1 between the workpieces abuts the belt conveyor 60 (see times t4 and t5).

As explained above, according to the embodiment-based sorting apparatus 1 the guide member 100F and the guide member 100R, equivalent to the transferring mechanism, project themselves from where these are housed further inside the endless belts 13A and 13B than the conveyance surface 10A that is the workpiece holding surface, the workpiece W held on the conveyance surface 10A for conveyance is pushed out to the conveyance route R3 or the conveyance route R4, rather than the workpiece W is caused to change its direction as a result of the end of the conveyed workpiece W being collided with the guide member 100F or the guide member 100R, so that the workpiece W is caused to transfer to the conveyance route R3 or the conveyance route R4.

As a result, the end of the workpiece W moves along the guide member 100F or the guide member 100R, and therefore, even when the workpiece W is configured of a soft material, it is possible to prevent the workpiece W from being bent or folded resulting from the collision with the guide and decrease a possibility of inconvenience such as the workpiece W cannot pass the sorting apparatus and thus jamming at the time of sorting. Moreover, the exact and smooth sorting is possible.

The guide member 100F and the guide member 100R configuring the transferring mechanism are disposed nearer to the center than the endless belt 13A and the endless belt 13B that act as the workpiece holding unit configured to hold the workpiece W across the direction CD perpendicular to the conveyance direction MD. The guide member 100F and the guide member 100R abut the area corresponding to the center of the workpiece W, i.e., a highly rigid portion out of the area where a plurality of unwoven fabrics are piled up, and thus, the workpiece W can be surely pushed out. As an example of a highly rigid portion, an absorber such as well known disposable diaper or sanitary napkin is preferred.

The sorting apparatus 1 according to this embodiment includes the guide member 100F and the guide member 100R capable of protruding toward the conveyance route R3 or the conveyance route R4 from the conveyance surface 10A that is the workpiece holding surface and the rotation supporting unit 110F and the rotation supporting unit 110R configured to rotatably support the upstream side ends 100Fa and 100Ra of the guide member 100F and the guide member 100R and rotate the guide member 100F and the guide member 100R.

With such a mechanism, in this embodiment, the guide member 100F and the guide member 100R can be made lighter, and the guide member 100F and the guide member 100R can be operated more responsively. Therefore, even if the high-speed conveyance of the workpiece W is introduced, the sorting can be surely performed while preventing the workpiece W from being bent or folded resulting from the collision with the guide and from being delayed for conveyance at the time of sorting.

In this embodiment, since there are provided the belt conveyor 60 configured to convey the workpiece W along the conveyance route R3 and at least one portion of the guide member 100R is arranged to face the abutment surface between the belt conveyor 60 and the workpiece W, the guide member 100R and belt conveyor 60 are continued, which avoids the riding up or folding of the downstream side end We positioned downstream of the conveyance direction of the workpiece W.

The belt conveyor 10 includes the blower 91 configured to blow air to the conveyance route R3 or the conveyance route R4 from the ventilation hole 94FA, the ventilation hole 94RA, the ventilation hole 94FB, and the ventilation hole 94RB formed at positions corresponding to the guide member 100F and the guide member 100R housed further inside the endless belts 13A and 13B than the conveyance surface 10A that is the workpiece holding surface.

Therefore, according to the embodiment-based sorting apparatus 1, at a timing at which the workpiece W held on the conveyance surface 10A for conveyance almost reaches the position of the guide member 100F or the guide member 100R, the guide member 100F or the guide member 100R is pushed out toward the conveyance route R3 or the conveyance route R4 and the air is blown to the conveyance route R3 or the conveyance route R4, enabling the workpiece W to smoothly transfer from the conveyance surface 10A to the conveyance route R3 or the conveyance route R4.

In this embodiment, the belt conveyor 10 includes the suction box 81 configured to suction external air via the endless belts 13A and 13B, inside the endless belts 13A and 13B. As a result, as shown in FIG. 1, the workpiece W can be surely conveyed while the belt conveyer 10 abuts the one surface of the workpiece W, and thus, the transferring mechanism (the guide member 100F or the guide member 100R) can be continuously disposed, enabling an increase in freedom in facility design.

In this embodiment, the belt conveyor 60 includes the suction box 83 inside the endless belt 64, and thus, even after sorting, the workpiece W, which is surely held for conveyance. Moreover, the air is cleaned or ventilated by the suction box 83 and the air blown from each of the ventilation holes is not easily reflected by the belt conveyor 60. As a result, the workpiece W can be more surely conveyed to the belt conveyor 60.

The workpiece W is transferred to the conveyance route R4 while the downstream side end We of the workpiece W abuts either one of the conveyance surface 10A that is the workpiece holding surface or the abutment surface (conveyance surface 60A) between the belt conveyor 60 and the workpiece W, and thus, the workpiece W will not float up from the conveyance route R4 and even after sorting, the workpiece W can be surely held for conveyance.

Another Embodiment

As described above, the content of the present invention has been disclosed through the embodiments of the present invention; it should not be understood that the description and the diagrams, one portion of the disclosure, restrict the present invention. From this disclosure, a variety of alternate embodiments, embodiments, and applicable techniques will become apparent to one skilled in the art.

For example, the embodiments of the present invention can be modified as follows: In the endless belts 13A and 13B, the through holes are formed, but the endless belts 13A and 13B may be structured to possess permeability such as a mesh structure.

In this embodiment, the shapes of the guide member 100F and the guide member 100R are plate-like, but the shapes of the guide member 100F and the guide member 100R are not limited. The shapes of the guide member 100F and the guide member 100R may be cylindrical or rod-like.

In this embodiment, as the sorting destination, the conveyance route R3 and the conveyance route R4 are prepared. However, one sorting destination may suffice. The configuration of the conveyance route (the belt conveyor 60 and the belt conveyor 70, for example) of the sorting destination such as the conveyance route R3 and the conveyance route R4 is not limited to that in the embodiment.

Thus, needless to say, the present invention includes a variety of embodiments not described here. Therefore, the technical scope of the present invention is only defined by the invention specific matters according to the claims reasonably derived from the above description.

The entire contents of Japanese Patent Application No. 2010-003435 (filed on Jan. 9, 2010) are incorporated in the present specification by reference.

INDUSTRIAL APPLICABILITY

According to the characteristics of the present invention, it is possible to provide a sorting apparatus capable to sorting the workpiece more surely and smoothly based on the workpiece's quality and other criteria even when the sheet-like workpiece so formed that a plurality of unwoven fabrics, constituent components of a disposable diaper and a sanitary napkin, for example, are piled up is conveyed at high speed.

The invention claimed is:
1. A sorting apparatus configured to sort out a workpiece by piling up a plurality of unwoven fabrics to a second conveyance route or a third conveyance route from a first conveyance route, the apparatus comprising:
 a conveyor mechanism configured to convey the workpiece from the first conveyance route to the second conveyance route while the workpiece is held, the conveyor mechanism having a workpiece holding surface configured to abut one surface of the workpiece; and
 a transferring mechanism configured to transfer the workpiece conveyed from the first conveyance route by the conveyor mechanism to the third conveyance route,
 wherein
 the third conveyance route is branched off from between the first conveyance route and the second conveyance route,
 the conveyor mechanism is continued over the first conveyance route and the second conveyance route,
 the transferring mechanism is configured to push out the workpiece held for conveyance by the conveyor mechanism from the workpiece holding surface toward the third conveyance route thereby to transfer the workpiece to the third conveyance route, and
 the transferring mechanism includes a ventilation unit configured to blow air from the workpiece holding surface toward the third conveyance route.

2. The sorting apparatus according to claim 1, further comprising a workpiece holding unit configured to hold the workpiece, wherein the transferring mechanism is provided nearer a center than the workpiece holding unit in a direction perpendicular to a conveyance direction of the workpiece.

3. The sorting apparatus according to claim 1, wherein the transferring mechanism includes:
a guide member capable of protruding from the workpiece holding surface to the third conveyance route; and
a rotation supporting unit configured to rotate the guide member, the rotation supporting unit rotatably supporting an upstream side end of the guide member.

4. The sorting apparatus according to claim 3, further comprising a sub conveyor mechanism configured to convey the workpiece along the third conveyance route,
wherein at least one portion of the guide member is configured to face a surface at which the sub conveyor mechanism abuts the workpiece.

5. The sorting apparatus according to claim 1, wherein the conveyor mechanism is configured to suction air via the workpiece holding surface.

6. The sorting apparatus according to claim 4, wherein the sub conveyor mechanism is configured to suction air via an abutment surface between the sub conveyor mechanism and the workpiece.

7. The sorting apparatus according to claim 1, wherein the transferring mechanism is configured to transfer the workpiece to the third conveyance route while a downstream side end of the workpiece positioned downstream of the conveyance direction abuts the workpiece holding surface.

8. The sorting apparatus according to claim 6, wherein the transferring mechanism is configured to transfer the workpiece to the third conveyance route while a downstream side end of the workpiece positioned downstream of the conveyance direction abuts the abutment surface between the sub conveyor mechanism and the workpiece.

* * * * *